(12) United States Patent
Janisse et al.

(10) Patent No.: US 9,897,821 B2
(45) Date of Patent: Feb. 20, 2018

(54) PROTECTIVE EYEWEAR

(71) Applicant: Warrior Sports, Inc., Warren, MI (US)

(72) Inventors: Richard J. Janisse, Windsor (CA); Jessica L. Hanson, Royal Oak, MI (US); James H. Lua, Columbus, OH (US); Sherry L. Jones, Pataskala, OH (US); Kevin J. Vititoe, Westerville, OH (US)

(73) Assignee: Warrior Sports, Inc., Warren, MI (US)

( * ) Notice: Subject to any disclaimer, the term of this patent is extended or adjusted under 35 U.S.C. 154(b) by 260 days.

(21) Appl. No.: 14/862,484

(22) Filed: Sep. 23, 2015

(65) Prior Publication Data

US 2016/0116759 A1    Apr. 28, 2016

Related U.S. Application Data

(60) Provisional application No. 62/067,596, filed on Oct. 23, 2014, provisional application No. 62/174,175, filed on Jun. 11, 2015.

(51) Int. Cl.
  *G02C 5/00* (2006.01)
  *A61F 9/02* (2006.01)
  *B29D 12/02* (2006.01)

(52) U.S. Cl.
  CPC .............. *G02C 5/001* (2013.01); *A61F 9/029* (2013.01); *B29D 12/02* (2013.01)

(58) Field of Classification Search
  CPC ........... A61F 9/029; G02C 5/045; G02C 9/02; A42B 3/20; A63B 33/002
  See application file for complete search history.

(56) References Cited

U.S. PATENT DOCUMENTS

| 2,212,014 | A | * | 8/1940 | Doyle | ..................... A61F 9/064 |
|---|---|---|---|---|---|
| | | | | | 2/8.1 |
| 2,504,524 | A | | 4/1950 | Hayward | |
| 2,758,308 | A | | 8/1956 | Ellis | |
| 3,457,564 | A | | 7/1969 | Holloway | |
| 4,067,069 | A | | 1/1978 | Slosek et al. | |

(Continued)

OTHER PUBLICATIONS

Great Atlantic Lacrosse Company Catalog, p. 63, Dec. 2008.

(Continued)

*Primary Examiner* — Tejash Patel
(74) *Attorney, Agent, or Firm* — Warner Norcross & Judd LLP

(57) ABSTRACT

Protective eyewear including a primary frame is joined with first and second separate and independent protective elements that can move relative to one another. The frame can be constructed from polymeric material, and can include a central portion and opposing left and right side portions that extend rearward to attachment elements and subsequently a strap. The protective elements can be in the form of metal cages, each including a perimeter element that generally surrounds a user's eye and a transverse element that reinforces the perimeter element. The protective elements are primarily only connected via the frame and can move relative to one another, optionally about a flex element defined by the frame. This can enable the eyewear to readily conform to a variety of different facial contours thereby meeting the demand of different players having different facial structure.

19 Claims, 6 Drawing Sheets

(56) References Cited

U.S. PATENT DOCUMENTS

| | | | |
|---|---|---|---|
| 4,077,068 A | 3/1978 | Anderson | |
| 4,264,987 A | 5/1981 | Runckel | |
| 4,527,291 A | 7/1985 | Nussbickl | |
| 4,991,952 A | 2/1991 | Grau | |
| 5,303,428 A | 4/1994 | Pernicka | |
| 5,313,665 A | 5/1994 | Luczenbacher, Sr. et al. | |
| 5,406,340 A | 4/1995 | Hoff | |
| 5,408,702 A | 4/1995 | Chiang | |
| 5,410,763 A | 5/1995 | Bolle | |
| 5,652,954 A | 8/1997 | Paiement et al. | |
| 5,706,526 A | 1/1998 | Huang | |
| 5,727,259 A | 3/1998 | Kawamata | |
| 5,799,338 A | 9/1998 | Huang | |
| 5,802,620 A * | 9/1998 | Chiang | A63B 33/002 2/428 |
| 5,802,622 A | 9/1998 | Baharad et al. | |
| 6,321,391 B1 | 11/2001 | Basso | |
| 6,349,420 B1 | 2/2002 | Chiang | |
| 6,449,777 B1 | 9/2002 | Montague | |
| 6,477,717 B1 | 11/2002 | Winefordner et al. | |
| 6,574,802 B2 | 6/2003 | Chiang | |
| 6,715,157 B2 | 4/2004 | Mage | |
| 6,817,068 B2 | 11/2004 | Cleary et al. | |
| 7,003,811 B2 | 2/2006 | Canavan | |
| 7,127,747 B2 | 10/2006 | Darnell et al. | |
| 7,162,750 B2 | 1/2007 | Canavan | |
| 7,222,959 B2 | 5/2007 | Jannard | |
| 7,322,692 B2 * | 1/2008 | Winningham | A61F 9/025 351/156 |
| 7,540,034 B2 | 6/2009 | Bologna | |
| 7,992,228 B2 | 8/2011 | Milea et al. | |
| 8,327,466 B2 | 12/2012 | Hahn et al. | |
| 8,782,821 B2 | 7/2014 | Brown | |
| 2004/0133958 A1 * | 7/2004 | Darnell | A63B 71/10 2/15 |
| 2005/0051164 A1 | 3/2005 | Hutter et al. | |
| 2010/0251465 A1 * | 10/2010 | Milea | A61F 9/027 2/452 |
| 2011/0078847 A1 * | 4/2011 | Hahn | A61F 9/029 2/431 |

OTHER PUBLICATIONS

Bugz Steel Mesh Safety Goggles, downloaded from http://www.westechrigging.com/bugz-goggles.html?productid=bugz-goggles&channelid=FROOG on Aug. 31, 2015.

STX Pitch Vision Field Hockey Goggle, downloaded from http://www.sportstop.com/Other_21/Eye-Protection_2/STX-Pitch-Vision-Field-Hockey-Goggle on Jul. 2, 2014.

* cited by examiner

PROTECTIVE EYEWEAR

BACKGROUND OF THE INVENTION

The present invention relates generally to protective sports equipment, and more particularly to protective eyewear for use during sports such as lacrosse and field hockey.

Lacrosse and field hockey are rough contact sports, and injuries to players are not uncommon. Such injuries can be caused by bodily contact with another player or by a player being struck with a stick. Contact with a lacrosse ball can also cause injuries because lacrosse balls are relatively heavy and travel at high speeds during play. As a result, players use a variety of protective equipment to avoid these injuries. For example, players typically use protective gloves, arm pads, shoulder pads, helmets and face guards.

Some types of protective equipment have been adapted specifically for male and female players. For example, male players often use helmets with wire cage face guards having metal bars welded together, while female players typically use a smaller protective eyewear device, such as goggles.

Conventional goggles typically include a single piece wire cage constructed from multiple metal bars welded to one another to form a network. The wire cage usually includes an open viewing area for disposal in front of both of a player's eyes so the wearer's field of view is relatively unobstructed. That metal cage can be fitted with some padding so that the cage does not rest directly against the player's face. The cushion can be configured for placement against the player's cheeks and forehead so that when the cage is impacted, the resulting force is attenuated with the padding before the force is transmitted to the wearer's face.

Goggle wire cages are usually rigid, extending across the wearer's face from left to right. Due to the rigid structure, the cage, and associated padding is usually non-deformable. Thus, the goggles sometimes only ergonomically fit a limited number of face types. For example, a goggle from one manufacturer having a wire cage well suited for a rounded, slim face, might not fit a flatter, wide face. Thus, individuals with the flatter, wide face might have to move to goggles from a different manufacturer. In some cases, a wearer may have to sacrifice comfort and fit for weight savings and viewing.

SUMMARY OF THE INVENTION

The present invention provides protective eyewear that is comfortable for a variety of players having different facial characteristics and that reliably maintains its position on a player's face and head.

In one embodiment, the protective eyewear includes a primary frame having a central portion and opposing sides. The central portion can define a flex element, optionally located midway between opposing sides of the frame. The primary frame may be constructed from a polymeric and/or elastomeric material so that the sides can flex relative to one another about the flex element. With this flexing, the eyewear can be comfortably fit to players having either narrow faces or wide faces, with the protective eyewear optionally bending or flexing to accommodate those different face types.

In another embodiment, the protective eyewear includes a first protective element and a second protective element, optionally in the form of cages, constructed from a rigid, durable material such as metal. The first and second cages can be joined with the frame and movable relative to one another about the flex element. The frame can include left and right side portions that merge into left and right temple portions. Optionally, the left and right side portions can be fixedly attached to the outer side members of the first and second protective elements so that those elements do not free float over those portions of the frame. This also can provide enhanced protection to the wearer due to the reduction of impact between the cages and the frame because those elements are attached to one another.

In still another embodiment, the first protective element and second protective element are separately constructed, independently formed metal cages that are separated from one another by a distance, yet connected or joined via the frame, and in particular, a bridge element of the frame. The first and second protective elements can be constructed from a homogenous metal material, optionally formed via a molding process. Suitable molding processes include metal injection molding (MIM), metal pour molding, investment casting and other suitable types of metal molding techniques.

In yet another embodiment, the first and second protective elements can be constructed to include a texture on an exterior surface thereof. This texture can include multiple projections and recesses which operatively can reduce glare transmitted to the player's eyes. In some cases, the exterior surface can include multiple diffuser ridges that redirect or diffuse glare so that it does not impinge upon the player's eyes.

In even another embodiment, the first and second protective elements can be specially formed so as to include a first surface or facet and a second surface or facet that transition to one another at a ridge, corner or apex. The surfaces can be angled or rounded in particular manner so as to reduce glare imparted to the player's eyes when the eyewear is used in unfavorable lighting conditions.

In a further embodiment, the protective elements can be constructed so as to include a first perimeter element that generally circumferentiates or surrounds a single one of the wearer's eyes, but optionally not both of the wearer's eyes. The perimeter element can be reinforced via at least one transverse element or bar extending from a first location of the first perimeter element to a second transverse location of the perimeter element, the second location being distal from the first location. Optionally, the transverse bar separates the viewing area defined within the first perimeter element into a major portion and a minor portion, with the minor portion being disposed laterally and outwardly, away from the eye and the nasal bridge of the player when the protective eyewear is worn.

In still a further embodiment, the first and second protective elements can include connector portions contiguous with or forming part of the perimeter element. The connector portion can be configured to be over molded by and optionally encapsulated by the primary frame, for example, the central portion thereof. The central portion of the frame can mechanically and chemically bond to the surfaces of the connector portions of the respective protective elements. In some cases, the connector portions can include the above-noted first and second facets that transition to one another, and optionally an interior facet that is joined with the above-noted facets. All of these facets, that is, the first and second facets, the transition between them, and the interior facet, can be substantially encapsulated by the frame at the connector portion of the respective protective element.

In yet another embodiment, the remainder of the first protective element, beyond the connector portions can be non-encapsulated by the frame and in particular the bridge element thereof. Of course, the outer left and right side members of the protective elements can be joined at an outer connection portion, directly to a lateral or side portion of the frame so that the protective element does not free float relative to the frame in those locations.

In another embodiment, the protective eyewear can include a secondary frame that is joined directly with the primary frame noted above. The secondary frame can generally include a central portion and left and right side portions. These portions can be molded directly to the corresponding central and left and right portions of the primary frame noted above.

In yet another, further embodiment, the protective eyewear can include a cushion or padding layer that is disposed on the interior of the secondary frame, or optionally the primary frame where the secondary frame is absent. This padding or cushion can be specially configured to extend down toward the cheek portions of the primary frame to absorb impact there, as well as across the brow of the player.

The current embodiments of the protective eyewear provide fit and form that accommodate a variety of differently structured face types. Where the flex element is incorporated into the primary or secondary frame, it can enable the separately constructed first and second protective elements to dynamically move relative to one another. Because the first and second protective elements are not formed as a single piece, rigid protective element, and are separated from one another, joined only with a polymeric and/or elastomeric bridge, these elements can move relative to one another about the flex element or some other axis region. Accordingly, the first and second protective elements can readily conform to a variety of different players' faces. Further, where the protective elements include textures and/or specially designed facets, the protective eyewear can reduce glare transmitted to the player's eyes. Thus, the eyewear can provide enhanced viewing, even in unfavorable lighting conditions.

These and other objects, advantages, and features of the invention will be more fully understood and appreciated by reference to the description of the current embodiment and the drawings.

Before the embodiments herein are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENTS

Figure 1:
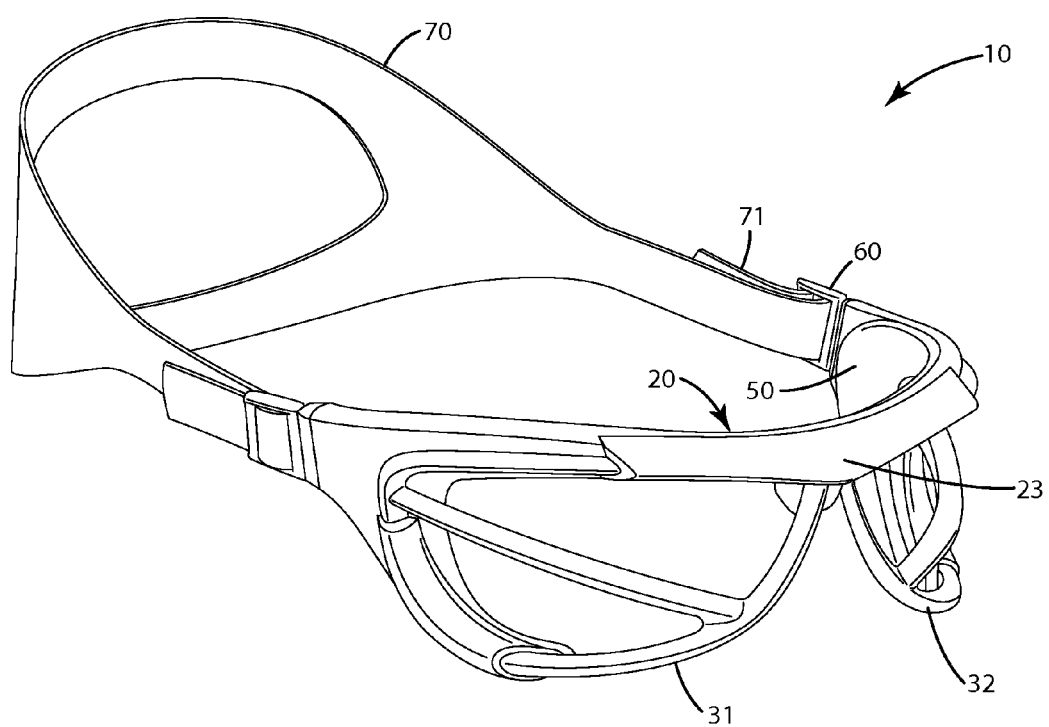
FIG. 1 is a front perspective view of a current embodiment of the protective eyewear.

Protective eyewear in accordance with a current embodiment is shown in FIGS. 1-7 and generally designated 10. The protective eyewear 10 generally includes a primary frame 20 that joins first and second protective elements 31 and 32, forming the functionally rigid portion of the protective eyewear 10. The primary frame 20 and first and second protective elements 31, 32 can be joined with a secondary frame 40. This secondary frame 40 can be located within or inside the primary frame and protective elements 31, 32. A padding or cushion layer 50 can be disposed interior of the secondary frame 30. This padding or cushion layer can include one or more pads as described in further detail below. The primary frame 20 can include one or more attachment elements 60 that secure one or more straps 70 to the frame, thereby enabling a player to secure the protective eyewear 10 to their heads, generally in front of their eyes. Optionally, the attachment elements can be formed as an insert molded into the primary or secondary frame, where the insert is of a harder durometers, and less flexible than the remainder of the frame.

Although described in connection with protective eyewear useful for sporting activities, such as lacrosse, field hockey and the like, the current protective eyewear can be used in a variety of other sports, such as soccer, ice hockey or any other sport that involves fast moving objects such as balls or pucks. Further, although described in connection with sporting activities, the protective eyewear can be used in occupational settings and/or in connection with military or law enforcement activities.

Further, for purposes of the current embodiment, "molded metal element" encompasses, but is not limited to, metal cages, protective elements and/or structures that are molded, formed and/or shaped from metal material, but excludes metal cages, protective elements or structures having bars that are welded to one another.

The structure and components described above now will be described in further detail, followed by a method of manufacturing the protective eyewear of the current embodiment. The protective eyewear is held on a player's head via a strap 70 engaging an attachment element 60 associated with the primary frame 20. The strap 70 can be constructed from an elastic material and can include a hole for accommodating a player's ponytail, if so desired. The strap 70 can include one or more ends 71, which can be laced or threaded through one or more slots, apertures or recesses 61, 63 defined by the attachment element 60. The straps ends 71 can be threaded through these slots, and overlapped with itself to provide a friction fit of the ends 71 relative to the attachment element 60. Other attachment mechanisms can be used to connect the strap 70 to the attachment element 60 and generally the primary frame 20. For example, the attachment element 60 can be modified to include a swivel element such as that disclosed in U.S. Pat. No. 7,992,228 or copending U.S. patent application Ser. No. 14/467,662. Optionally, if desired, the attachment element 60 and part of the primary frame 20 can be connected to a head gear shell, which can include a soft shell and/or a hard shell that covers an upper portion of the player's cranium (not shown).

Figure 5:
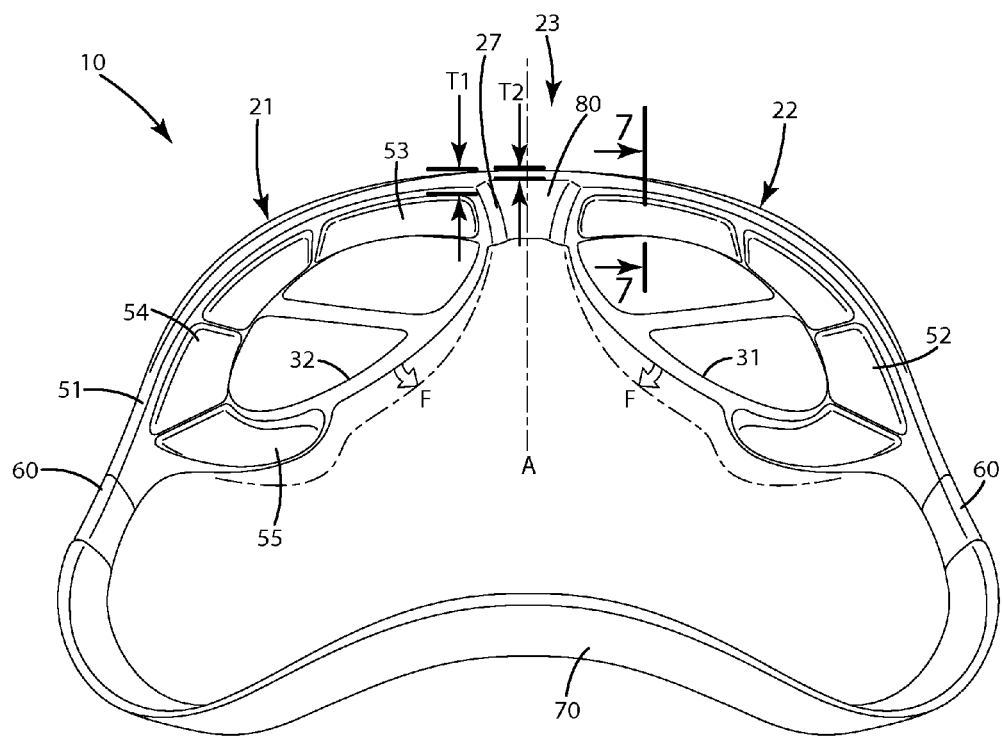
FIG. 5 is a rear perspective view of the protective eyewear.

The cushion or padding element 50 can be one piece, or can be separated into first 51 and second 52 padding parts. These parts can be constructed from any suitable compressible layer, for example, an elastomer or knit layer, a gel, woven or nonwoven fabric, and/or open or closed cell foam. If an elastomer, that construction can be over molded or adhered to the inner parts of the secondary frame 40, or where absent, directly to the interior surfaces of the primary frame 20. As shown in FIG. 5, first and second padding parts 51, 52 can include a brow portion 53 that extends outward and merges with temple portions 54. The temple portion can gradually extends downwardly under at least a portion of the protective elements 31, 32, to form a padded cheek portion 55. This cheek portion can extend over the cheek bone, for example, the zygomatic bone.

Optionally, the first and second padding parts 51, 52 are separated by a gap G and generally disconnected from one another. This gap can accommodate a flex element 80 in conjunction with the primary frame 20 and/or secondary frame as further described below. The pad elements can have a textured surface, if desired, with raised portions contacting a player's skin. If desired, performance fabric can be included in the padding elements to provide additional comfort and grip relative to the player's face.

Turning now to the primary frame 20, it can include a central portion 23, and left 21 and right 22 brow portions that extend laterally outwardly from the central portion 23. These brow portions 21 and 22 can extend outwardly to the first lateral side portion 25 and the second lateral side portion 26 of the primary frame 20. These portions themselves can extend downwardly along, and toward the cheekbones of a player, generally following the protective elements 31 and 32. The attachment element 60 of the frame can extend rearward of these first and second lateral side portions.

The central portion 23 can be in the form of an elongated bridge adapted to extend across a player's brow above a wearer's nose. Optionally, the bridge can be configured to span above the player's nasal bridge. This elongated bridge or central portion 23 can include an interior 27. The interior 27 of the primary frame 20 can define or include a flex element 80. Generally, the flex element 80 can be centered on a central axis A of eyewear 10. The central axis A can generally bisect the goggles into equally sized left and right portions. Optionally, the flex element 80 can be defined by or included in an interior the secondary frame 40 in addition to or instead of being defined by and/or included in the primary frame 20. Further optionally, the flex element 80 can be an area or region of the primary and/or secondary frames that is constructed from a flexible material, thereby allowing the first and second cages to articulate relative to one another. The flex element itself need not be an independent part; instead, it can be a portion of the primary and/or secondary frame having bending and/or flexing properties, so that the cages can articulate relative to one another, optionally about the pivot axis. As a further example, the primary frame and/or secondary frame can be constructed from a rubber or elastomeric material in the region of the flex element 80. As another example, in this region the primary and/or secondary frames can simply be thinner than other adjacent portions on opposing sides of those frames. Either way, the flex element can enable the opposing left and right sides of the goggles to move and/or articulate relative to one another, and specifically to enable and/or allow the first and second cages to move relative to one another in a predetermined manner.

Yet further optionally, the flex element 80 as illustrated can include a recess or depression located on the interior 27 of the bridge element 23. This recess can be a reduction in thickness from an overall thickness T1 to a lesser thickness T2 in the frame in the region associated with flex element. Optionally, the thickness reduction can be primarily in the secondary frame 40. As an example, the central portion 23 can be of a uniform thickness from left to right across the wearer's brow. The secondary frame 40 however can define the flex element which can be in the form of a recess on the interior 27 thereof. In turn, this can reduce the overall thickness of the secondary frame relative to the remainder of the secondary frame.

Further optionally, the flex element 80 can be in the form of a series of slots placed one adjacent the other to form a portion of weakness in the primary frame 20 and/or secondary frame 40. Even further optionally, the flex element 80 can be in the form of a hinge (not shown) that connects the left and right portions of the frame. The hinge can include one or more pins that pivotally secure the left and right portions of the frame to one another.

As shown in FIG. 5, the eyewear 10 is constructed so that the primary and/or secondary frame can effectively flex and pivot about the central axis A. More particularly, as the strap 70 is pulled taut, for example, around a player's head, the first and second protective elements 31 and 32 can flex in direction F generally toward one another or away from one another depending on the particular facial features of the player. With a narrower face, the elements 31 and 32 as well as the left and right brow portions 21 and 22 of the primary frame, flex generally toward one another in direction F. With a wider face, these elements can optionally flex in an opposite direction, away from one another, opposite the direction of the arrows F. This flex element, in conjunction with the independently and separately constructed first and second protective elements 31 and 32, facilitates the flexing of the eyewear and its subsequent conformance to the contours of a player's face, whether the wearer has a wide face or a narrow face.

Figure 2:
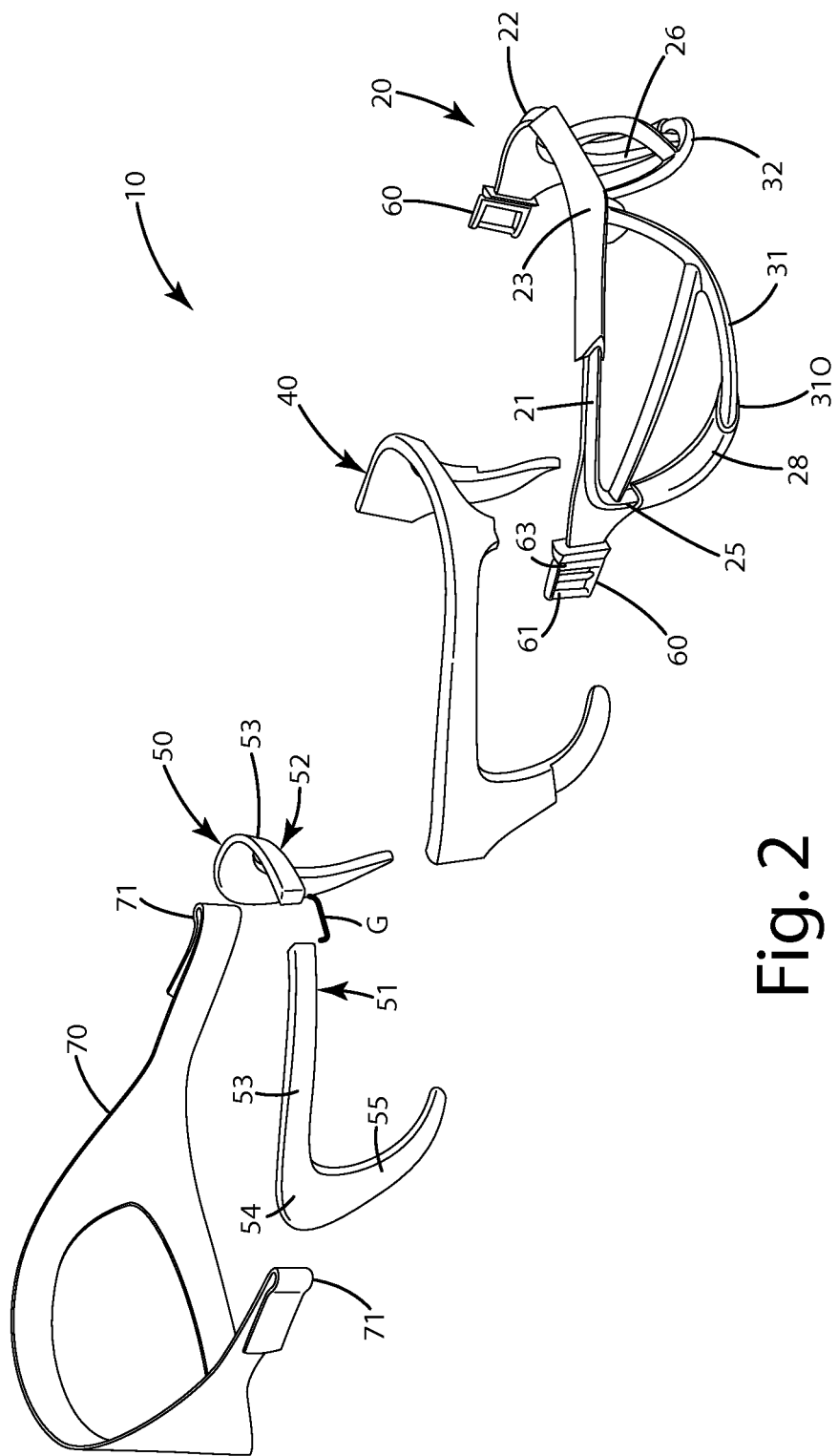
FIG. 2 is an exploded perspective view of the protective eyewear.
Figure 3:
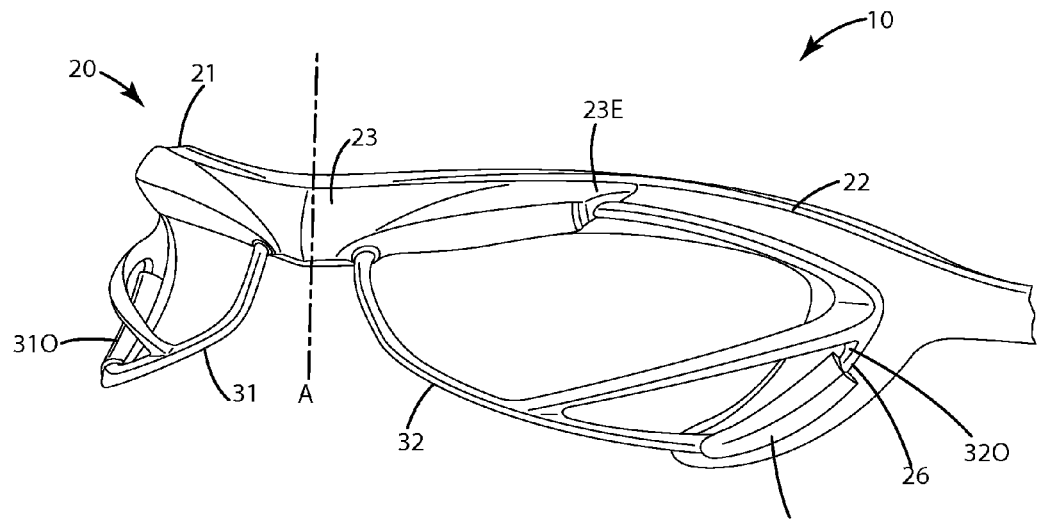
FIG. 3 is a close up front perspective view of the protective eyewear.

With reference to FIGS. 2, 3 and 5, the primary frame 20 can be generally constructed from one or more polymeric materials, which also encompasses elastomeric materials such as TPU, as well as natural and synthetic rubber, and/or silicone based materials. The central portion 23 can be constructed so that it projects outwardly, generally over at least portions of the first and second protective elements 31, 32. The central portion 23 can merge into the first and second brow portions 21 and 22. The primary frame 20 can be constructed so that the central portion 23 covers the protective elements 31, 32 from a location near the central axis A to a portion about $\frac{1}{3}$, $\frac{1}{2}$ and/or $\frac{3}{4}$ the distance away from the central axis A along the respective protective elements. The central portion 23 can terminate at a terminating end 23E. At this terminating end 23E, a portion of the protective elements 31, 32 can extend outwardly from the primary frame. The portions of the protective elements under or within the central portion 23 of the primary frame can be concealed, while beyond the end 23E, the remaining portions of the protective elements can be exposed and unconcealed.

The remaining portions of the protective elements can extend along and adjacent the left and right brow portions 21, 22 of the frame. In these regions, the protective elements can contact the brow portion of the frame, but are not encapsulated in these brow portions. Near the outer side members 31O, 32O of the protective elements 31, 32 (FIG. 3) the protective elements 31, 32 can be secured to the lateral portions 25, 26 of the primary frame 20. In this manner, the protective elements 31 and 32 are fixedly secured at their outer side members 31O, 32O directly to the respective first and second lateral side portions 25, 26 of the frame so that the first side member and the first side portion, as well as the second side member and second side portion, move together, in unison.

Optionally, upon movement of the first and second protective elements, the outer side members 31O, 32O and the side portions 25, 26 of the frame move together in unison about the flex element and generally about the central axis A of the protective eyewear 10. The outer side members of the protective elements can be secured to the primary frame, via an outer connector portion 28 that extends outwardly from the lateral side portions 25, 26 of the frame 20.

As shown in FIG. 3, this outer connector portion 28 extends from lateral side portion 26 and generally envelops and substantially encapsulates and/or conceals the outer side members 31O, 32O of the protective element 32. This connector portion 28 of the frame can be located downwardly on the portion of the frame adjacent the cheek and/or temple of the player. Optionally, the connector portion can encapsulate and/or conceal the outer side members from the lowermost portion of the protective elements to the intersection of the side members with the transverse member 38, or even above that, so the connector portion covers and encapsulates the upper brow portion 35.

The above encapsulation also facilitates the attachment of the protective elements along their outermost portions directly to the primary frame. In this manner, the protective elements are prevented from free floating or otherwise forming a gap between the lateral side portions of the frame 25, 26 and the different portions of the protective elements 31 and 32. In this manner, the protective elements can always maintain contact with and can be immediately adjacent the different components of the frame, even when conformed closely to the contours of a player's face.

Optionally, the other portions of the protective elements 31 and 32 not captured and secured to the frame via the bridge element 23 and/or connector portions 28 can be exposed to the environment.

As mentioned above, the protective eyewear shown in FIGS. 2-4 includes protective elements 31 and 32. For purposes herein, only the right protective element 32 will be described. It will be appreciated that the other or left protective element 31 can be a mirror part of the element 32, and similar in structure, function and properties. Generally, the protective element 32 includes a perimeter element 33. The perimeter element 33 includes an upper brow portion 35 that merges into an interior or nasal portion 36. The nasal portion 36 transitions to a lower perimeter portion 37 which transitions to the outer side member 32O of the protective element 32. This outer side member then transitions back to the brow portion 35 of the perimeter element 33. Generally, the upper brow portion, nasal portion, lower perimeter portion and outer side member 32 form a continuous, slightly polygonal or elliptical shape. The shape is configured so that it encircles or generally surrounds a player's eye E to provide protection generally to the eye.

The perimeter element 33 can be reinforced by a transverse element or bar 38. The transverse element 38 can extend from a first location 33A to a second distal location 33B along the perimeter element 33. These locations 33A and 33B can be separated from one another by approximately one to three inches. The transverse element can be shorter in length from the first location 33A to the second location 33B than the perimeter element 33 spanning between those same locations 33A and 33B. Optionally, the transverse bar 38 can project outwardly away from the wearer's face slightly more than the brow portion 35 and/or the lower perimeter portion 37. This can provide additional impact absorption and protection to the wearer's eye E. Further optionally, the first location 33A can be somewhere along the brow portion and/or outer side member, and the second location 33B can be somewhere along the lower perimeter portion and/or nasal portion.

Figures 6, 7:
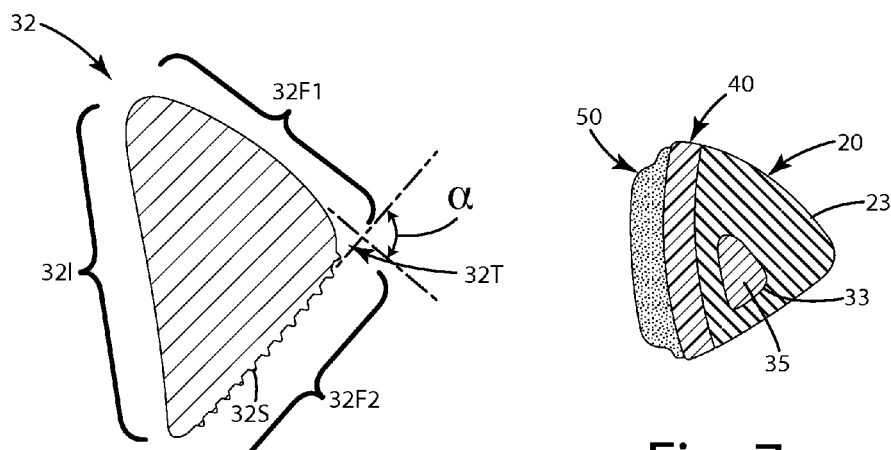
FIG. 6 is a cross section taken along lines 6-6 of FIG. 4 of the protective element.
FIG. 7 is a cross section taken along lines 7-7 of FIG. 5 of a primary frame, secondary frame and the protective element.

The protective element 32 can be constructed so that the perimeter and/or transverse element have unique contours and surface configurations. For example, as shown in FIG. 6, the protective element 32 can include an interior surface 32I. This interior surface can face toward the face of a player. Opposite that interior surface 32I, the protective element 32 can include one or more facets or surfaces 32F1, 32F2. These facets or surfaces can be planar, rounded or of any other convex, concave or other shape, depending on the particular application. The facets 32F1 and 32F2 can be configured to reduce the amount of glare that is transmitted back toward the player's eye E.

As illustrated in FIG. 6, the first facet 32F1 can transition at a transition region 32T to the second facet 32F2. These facets can be disposed at an angle $\alpha$ relative to one another. This angle $\alpha$ can optionally range from about 1° to about 180°, further optionally about 10° to about 90°, even further optionally about 30° to about 55°, yet further optionally about 45°. The particular transition region 32T can be rounded, angled or stepped, depending on the particular application, to transition between the first facet 32F1 and the second facet 32F2. The facets 32F2 and 32F1 can be of the same length, same dimension or different dimensions. For example, the facet 32F1 can be less than the length of the facet 32F2 shown in the cross section of FIG. 6. This can enable the facet 32F2, which is closer to the eye E of the player, to be at a sufficient angle to redirect glare caused by sun or artificial lighting away from the user's eye.

As further illustrated in FIG. 6, optionally one or more of the facets can include a special glare reducing surface treatment 32S. This surface treatment can in the form of a glare reducing film, coating and/or surface. As an example, it can include multiple nodes, projections and/or valleys that absorb, diffuse, reflect or otherwise prevent glare or light from being reflected to or toward the player's eye E. In some cases, the surface 32F2 can be ground, anodized, e-coated, and/or roughened to provide the surface treatment. Again, this can assist in reducing glare or light from being reflected toward the player's eye E from the outer facing surfaces of the protective element 32.

Figure 8:
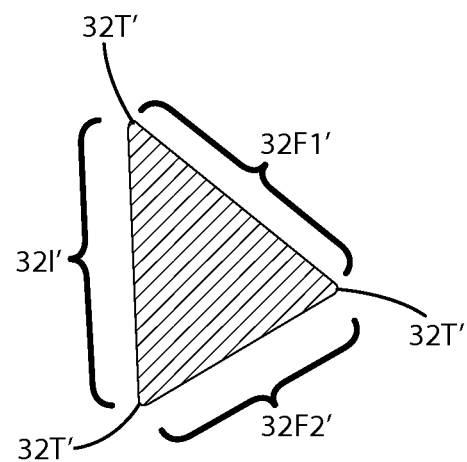
FIG. 8 is a cross section of a first alternative embodiment of the protective element taken along lines 6-6 of FIG. 4.
Figure 9:
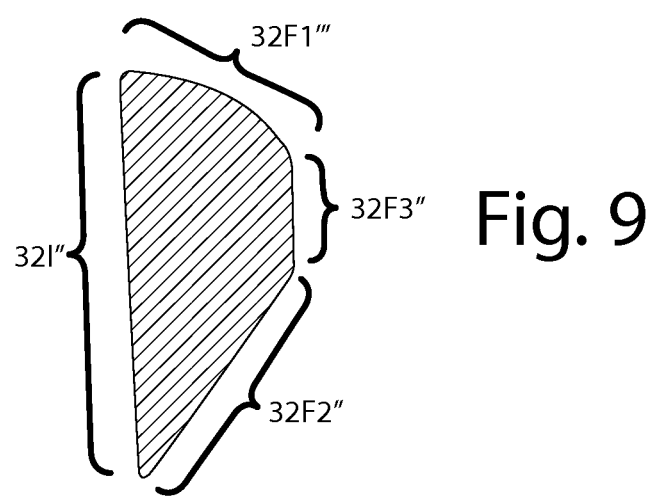
FIG. 9 is a cross section view of a second alternative embodiment of the protective element taken along lines 6-6 of FIG. 4.

Alternative constructions of the protective elements are contemplated. For example, a first alternative construction of a cross section of the protective element is illustrated in FIG. 8. This embodiment is similar to the embodiment above except the interior surface 31I', first facet 32F1' and second facet 32F2' transition at angled regions 32T' relative to one another. The angles selected for these transitions can be the same as angle α mentioned above in connection with the transition 32T. In this embodiment, these transitions 32T', however, are not rounded, and instead are relatively pointed, which can provide a different aesthetic appearance of the protective element. In a second alternative embodiment of the cross section of the protective element is illustrated in FIG. 9. There, the protective element includes a first interior surface 32I", which transitions to a rounded second planar facet 32F1" on the top and a second facet 32F" on the bottom. These facets, however, are separated from one another, but connected by a planar or rounded third facet 32F3". More or fewer facets, of varying contours, can be utilized depending on the particular application.

Figure 11:
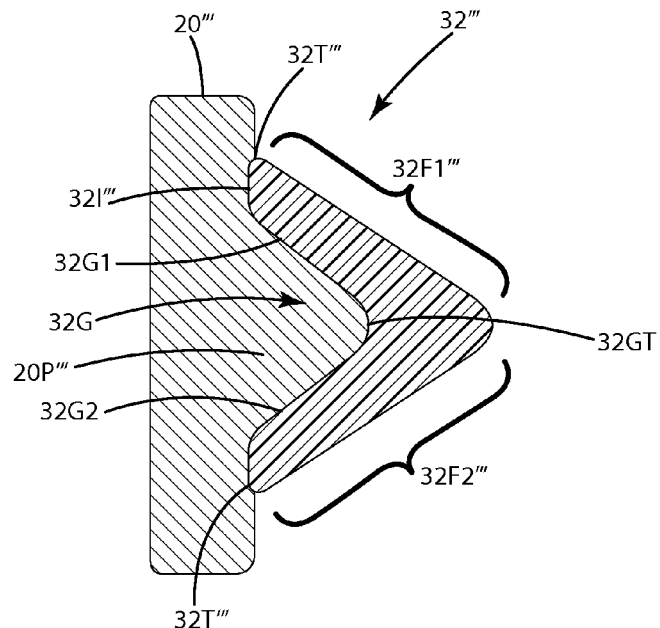
FIG. 11 is a cross section of a first alternative embodiment of the protective element taken along lines 6-6 of FIG. 4.

Another example of the protective element is illustrated in FIG. 11. There, a third alternative embodiment of the cross-section of the protective element is shown. The protective element 32''' can include an interior facing surface 32I''', which transitions at rounded corners 32T''' to first and second forward facing facets 32F1''' and 32F2'''. The interior facing facet or surface 32I''' can define a groove or recess 32G. This groove 32G generally can face toward the player when the eyewear is donned. The groove 32G can be disposed between the transition portions 32T''' adjacent the interior surface 32I'''. In some cases, the groove can extend all the way to the transition portions, while in other cases the groove can terminate a predetermined distance inward from the transition portions, depending on the application.

In effect, the groove 32G can reduce the amount of material used to construct the cage, which in turn can provide improved weight savings for the cage. In addition, the groove can add structural rigidity to the cage. In some cases, it is desired that the groove 32G be concealed. Accordingly, the primary frame 20''' can be molded over a portion of the cage 32''' and in particular the interior surface 32I''' so that the groove is substantially concealed in the finished product. With this construction, the primary frame can form a projection 20P''' that projects into and substantially fills the groove 32G. The material from which the projection is formed can bond directly to the services 32G1 and 32G2 of the groove 32G. In some embodiments, the groove can be formed as a continuous groove extending along a portion of the cage. In other embodiments, the groove can be formed as multiple intermittent smaller grooves along a portion of the cage. It is also contemplated that the groove can be formed in the forward facing facets of the cage, and some cases may not be concealed by another element of the goggle.

Returning to the current embodiment at FIGS. 1-6, the protective element 32 generally forms ridges at the transition regions 32T along each of the perimeter elements and transverse elements. These ridges face outward, away from the player's face and can have a polygonal (e.g. triangular) or rounded shape. With this shape, rigidity is added to the protective element while still preserving an adequately wide impact absorbing interior surface 32I. The interior surface 32I can be sufficiently broad to disperse forces exerted at the ridge and transferred generally through the protective element. The ridges at the transition regions 32T of the respective transverse element and perimeter element optionally can merge together smoothly at the first and second locations 33A and 33B. Of course, if desired, the ridges of these elements can flatten, and can generally transition to one another at a flat area where they meet.

Figure 4:
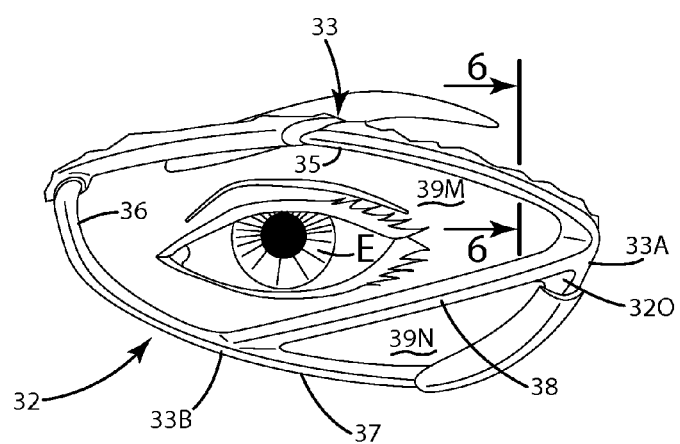
FIG. 4 is a close up view of a protective element used in connection with the protective eyewear.

As shown in FIGS. 4 and 5, each of the respective protective elements 31, 32 are separately constructed from one another. Optionally, before their connection to the frame 20, these elements are independent pieces and do not and are not connected in any way to one another. Each of the respective protective elements 31 and 32 is configured to protect respective left and right eyes of the wearer. Each of these elements separately surround individual ones of the user's eyes, in contrast to a single unit that surrounds both of the user's eyes simultaneously. Thus, each protective element is dedicated to each respective eye of the player.

As shown in FIG. 4, the protective elements also are separated into major 39M and minor 39N viewing apertures or portions. The major viewing aperture 39M is configured to be placed immediately adjacent the player's eye and the player uses that as the primary area through which to view objects and the surrounding environment. The minor viewing aperture or portion 39N generally is not used extensively for viewing. Although in some cases, the player can easily view through that portion 39N by looking laterally downward. The lateral side portions of the frame can be diminutive enough to ensure that when a player does view through the minor viewing portion 39N, they can still see through that portion without too much obstruction by the outer connector portions 28.

The protective elements are joined independently with the primary frame 20. As illustrated in FIGS. 3 and 7, the protective elements along the brow perimeter elements 35 are each joined directly with the bridge or central portion 23 of the frame 20. As shown in FIG. 7, the brow portion 35 of the perimeter element 33 is substantially encapsulated and embedded within the material from which the central portion 23 is constructed. The central portion 23 can be constructed from a polymeric, elastomeric or plastic material that is over molded over all of the surfaces of the protective element along at least part of the brow portion 35 and/or the nasal portion 32 of the protective element. In this manner, the protective element is physically and chemically bonded directly to the primary frame and, in particular, the bridge element 23. As shown in FIG. 7, all of the first, second and interior facets of the protective element are substantially enveloped by the and encapsulated by the polymeric material of the central portion 23. This can ensure that the protective element does not rotate or move relative to the frame. Optionally, for the central quarter, third, half of the brow portion 35 of the protective elements, the perimeter element 33 is encapsulated substantially entirely and concealed from view by the bridge element 23. Optionally, this bridge element can extend farther out toward the left and right lateral side portions of the frame 22 encapsulating as much of the brow and/or other portions of the perimeter element as desired, depending on the particular application.

As further shown in FIG. 7, the optional secondary frame 40 can be molded, adhered or otherwise fastened to the primary frame 20. The padding elements 50 also are joined to the optional secondary frame 40 via direct molding, fastening or adhesion. Of course, the secondary frame can be deleted from the construction, and the padding 50 joined directly to the primary frame 20.

The protective elements 31 and 32 and the components thereof are typically constructed from metal, independently and separately from one another in separated mold cavities of a mold. Optionally, these components can be molded from metal, for example, using metal injection molding (MIM) processes, investment casting and/or these components can be forged, milled or machined from metal blanks. Generally, the metal that forms these protective elements is a homogeneous material with generally consistent density on molecular makeup throughout. The components of the protective elements can be substantially entirely integral and one piece, which means that they are not previously constructed from different parts (other than at a molecular level) that are joined, fastened or otherwise attached to one another. Different metals suitable for use in construction of the protective elements include steel, titanium, scandium, aluminum, magnesium, alloys, and other metals. Optionally, the elements 31, 32 can have a protective coating, such as rubber or a synthetic material, and can be finished to remove any sharp edges that could cut a player.

Figure 10:
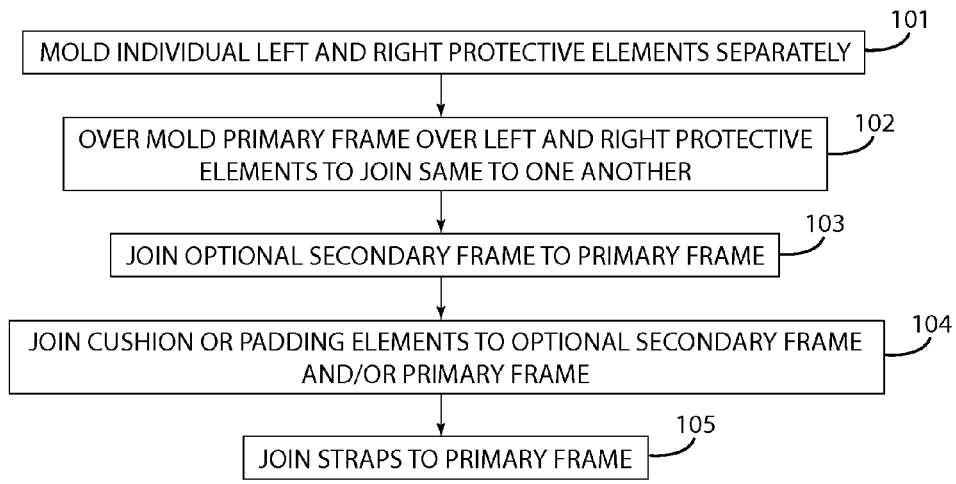
FIG. 10 is a block diagram illustrating method of making the protective eyewear of the current embodiment.

Generally, the protective eyewear described herein can be constructed using the methods shown in the illustration at FIG. 10. The individual left and right protective elements 31 and 32 are molded, formed or otherwise produced in step 101. As mentioned above, these elements can be formed with different structural components such as the different facets, ridges, perimeter elements, transverse elements (which can vary by number and depending on the application). After these individual protective elements formed, optionally in a first mold, they are removed from that mold and moved to a second mold. In this second mold, step 102 is performed in which the primary frame 20 is molded over selected portions of the left and right protective elements 31 and 32, to join those elements to one another. During this over molding, the central portion of the frame over molds and chemically and physically bonds directly to the various interior and exterior facets of the respective protective elements 31 and 32, thereby encapsulating them. This joins the respective protective elements to the primary frame. In this step 102, the outer connector portions 28 optionally are molded over the respective portions of the side members of the protective elements to secure the outer portions thereof so that the protective elements do not free float relative to the frame. When the primary frame is formed, the flex element also can be formed in it, as an integral portion of the frame itself, or later in the optional secondary frame.

With the primary frame and its components molded directly to the protective elements, the secondary frame optionally can be joined with the primary frame in step 103 if the secondary frame is included in the construction. This can be accomplished by removing the primary frame and protective elements from the second mold and placing them in a third mold, then molding the secondary frame over the rear or interior portion of the primary frame. Optionally, where the primary frame is the only frame in the goggles, the foregoing step can be eliminated. In step 104, the cushion or padding elements 51 and 52 can be joined with the secondary frame and/or primary frame. Thereafter, the straps 70 can be further joined with the primary frame to complete the eyewear. Further finishing and packaging may be performed to prepare the eyewear for distribution and/or transport.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A protective eyewear comprising:
  a frame including an elongated bridge adapted to extend across a player's brow adjacent a wearer's nose, the elongated bridge including an interior adapted to face a player's face, and an exterior opposite the interior, the elongated bridge defining a flex element generally centered over the player's nose, the frame including first and second lateral side portions;
  a first protective element joined with the elongated bridge on a left side of the player's head and adapted to surround a player's left eye;
  a second protective element joined with the elongated bridge on a right side of the player's head and adapted to surround a player's right eye;
  a cushion element joined with at least one of the elongated bridge, the first protective element and the second protective element, the cushion element adapted for disposition between the player's face and the respective first protective element and the second protective element,
  wherein the first protective element and the second protective element are separately and independently formed from metal, separated from one another by a distance, and independently movable relative to one another about the flex element,
  whereby the protective eyewear readily conforms to a player's facial contours,
  wherein the first protective element includes a first side member,
  wherein the first side member is secured to the first lateral side portion of the frame so that the first side member and first side portion move together, in unison, upon movement of the first and second protective element about the flex element.

2. A protective eyewear comprising:
  a frame including an elongated bridge adapted to extend across a player's brow adjacent a wearer's nose, the elongated bridge including an interior adapted to face a player's face, and an exterior opposite the interior, the elongated bridge defining a flex element generally centered over the player's nose, the frame including first and second lateral side portions;

a first protective element joined with the elongated bridge on a left side of the player's head and adapted to surround a player's left eye;

a second protective element joined with the elongated bridge on a right side of the player's head and adapted to surround a player's right eye;

a cushion element joined with at least one of the elongated bridge, the first protective element and the second protective element, the cushion element adapted for disposition between the player's face and the respective first protective element and the second protective element, wherein the first protective element and the second protective element are separately and independently formed from metal, separated from one another by a distance, and independently movable relative to one another about the flex element, wherein the first protective element and the second protective element are each metal injection molded parts, wherein the first protective element includes a first facet and a second facet disposed at a first angle relative to one another, the first facet and the second facet joined at a ridge that is at least one of rounded and angled so that the first facet and second facet transition to one another, wherein the second facet is oriented to prevent glare from being directed from the first protective element toward the player's left eye.

3. A protective eyewear comprising:

a frame including an elongated bridge adapted to extend across a player's brow adjacent a wearer's nose, the elongated bridge including an interior adapted to face a player's face, and an exterior opposite the interior, the elongated bridge defining a flex element generally centered over the player's nose, the frame including first and second lateral side portions;

a first protective element joined with the elongated bridge on a left side of the player's head and adapted to surround a player's left eye;

a second protective element joined with the elongated bridge on a right side of the player's head and adapted to surround a player's right eye;

a cushion element joined with at least one of the elongated bridge, the first protective element and the second protective element, the cushion element adapted for disposition between the player's face and the respective first protective element and the second protective element, wherein the first protective element and the second protective element are separately and independently formed from metal, separated from one another by a distance, and independently movable relative to one another about the flex element, wherein the first protective element is of an elongated oval shape, wherein the first protective element includes a first outer side member joined with a first lower perimeter member that extends toward a first nasal portion, away from the first side member.

4. The protective eyewear of claim 3 wherein the first protective element includes a first transverse bar extending from the first outer side member to the first lower perimeter member, the first transverse bar dividing the elongated oval shape into first and second portions, the first portion being larger than the second portion, the first portion forming a primary viewing aperture through which the player views using a left eye of the player.

5. The protective eyewear of claim 4 wherein the first outer side member, first lower perimeter member and first transverse bar are integrally formed with one another as a molded metal element and from a metal injection molding process.

6. A protective eyewear comprising:

a frame including central portion and opposing lateral side portions;

a first cage joined with the frame and adapted to protect a first eye of the player, the first cage being a unitary, one piece molded metal element, the first cage including a first perimeter element generally surrounding the first eye, the first cage including a first transverse bar extending from a first location along the first perimeter element to a second, distal location along the perimeter element so as to form a first and a second viewing aperture in the first cage;

a second cage joined with the frame distal from the first case and adapted to protect a second eye of the player, the second cage being a unitary, one piece molded metal element, the second cage including a second perimeter element generally surrounding the second eye, the second cage including a second transverse bar extending from a third location along the second perimeter element to a fourth, distal location along the second perimeter element so as to form a third and a fourth viewing aperture in the second cage; and wherein the first and second cages are separately constructed, and joined via the frame.

7. The protective element of claim 6 wherein the frame is constructed from a polymeric material that encapsulated portions of the first and second cages.

8. The protective eyewear of claim 6 wherein the first and second perimeter elements and the first and second transverse bars each include a surface treatment that reduces glare perceived by the player.

9. The protective eyewear of claim 6 wherein the first perimeter element and first transverse element each include a first facet and a second facet that merge into one another along an exterior ridge that faces outward, away from the player's face.

10. The protective eyewear of claim 6 wherein the frame defines a recess above a nasal bridge of the player, the recess providing a flex element adapted to flex, whereby the first and second cages move relative to one another when the flex element is flexed.

11. The protective eyewear of claim 6 wherein the frame includes a bridge element constructed of at least one of a polymeric material and an elastomeric material that encapsulates a first minor portion of the first cage and a second minor portion of the second cage.

12. The protective eyewear of claim 6:

wherein the first perimeter element includes a lower perimeter portion, and an outer side member, where the first transverse bar extends from the lower perimeter portion to the outer side member, wherein the outer side member is secured to a side of the frame so that the outer side member is non-free floating relative to the frame.

13. The protective eyewear of claim 6 comprising:

a secondary frame joined with the frame, the secondary frame located between the frame and player's face, and a cushion element joined with the secondary frame, the cushion element positioned to engage the player's face.

14. The protective eyewear of claim 6,
wherein the first perimeter element includes a first perimeter element ridge,
where the first transverse bar includes a first transverse bar ridge,
wherein the first perimeter element ridge and first transverse bar ridge transition to one another at a ridge intersection.

15. A method of manufacturing protective eyewear comprising:
providing a first cage adapted to protect a first eye of a player, the first cage being a first unitary, one piece molded metal element, the first cage including a first perimeter element generally surrounding the first eye, the first cage including a first transverse bar extending from a first location along the first perimeter element to a second, distal location along the first perimeter element so as to form a first and second viewing apertures in the first cage;
providing a second cage adapted to protect a second eye of the player, the second cage being a second unitary, one piece molded metal element, the second cage including a second perimeter element generally surrounding the second eye, the second cage including a second transverse bar extending from a third location along the second perimeter element to a fourth, distal location along the second perimeter element so as to form a third and fourth openings in the second cage;
molding a polymeric material over a first portion of the first cage and a second portion of the second cage to form a polymeric frame that joins the separately constructed first cage and second cage.

16. The method of claim 15 wherein the first perimeter element includes a first nasal portion and a first side member, comprising joining the first side member to the frame so that the first cage moves with the frame.

17. The method of claim 15 comprising forming a flex element in the polymeric frame, the flex element generally located above the player's nasal bridge when the eyewear is worn by the player.

18. The method of claim 15 comprising forming a first textured surface on an outer facet of the first cage, the first textured surface adapted to reduce glare from transferring to a player's eyes.

19. The method of claim 15 comprising:
joining a secondary frame to a rearward surface of the polymeric frame;
extending the secondary frame adjacent the first and second perimeter elements; and
joining a cushion element to the secondary frame, the cushion element adapted to engage the wearer's face.

* * * * *